United States Patent [19]
Demian et al.

[11] Patent Number: 6,063,925
[45] Date of Patent: May 16, 2000

[54] SEPARATION OF ENANTIOMERS OF OCTAHYDROISOQUINOLINE

[75] Inventors: Iulia Demian; Kenneth D Stanley, both of Richmond, Va.

[73] Assignee: B.I. Chemicals, Inc., Petersburg, Va.

[21] Appl. No.: 09/146,124

[22] Filed: Sep. 2, 1998

Related U.S. Application Data

[60] Provisional application No. 60/059,193, Sep. 17, 1997.

[51] Int. Cl.[7] ................................................. C07D 217/20
[52] U.S. Cl. .............................................. 546/149
[58] Field of Search ............................................ 546/149

[56] References Cited

FOREIGN PATENT DOCUMENTS

| | | |
|---|---|---|
| 176856 | 4/1986 | European Pat. Off. . |
| WO 9703052A | 1/1997 | WIPO . |

OTHER PUBLICATIONS

Chemical Abstracts, vol. 88, No. 1, Jan. 2, 1978, abstract No. 6751j, p. 573.

A. Brossi et al.: "Hydroxy–morphinane Versuche zur Racemisierung Optisch Aktiver 1–(p–hydroxybenzyl)–1,2,3,4,5,6,7,8–oxtahydro–isochinoline"—Helvetica Chimica Acta., vol. 39, 1956, pp. 1376–1386, XP002085621; pp. 1376, 1377, 1381.

*Primary Examiner*—John Kight
*Assistant Examiner*—Charanjit S. Aulakh
*Attorney, Agent, or Firm*—Robert P. Raymond; Alan R. Stempel; Mary-Ellen M. Devlin

[57] ABSTRACT

This invention describes a process for the isolation of (−)1-(p-methoxybenzyl)-1,2,3,4,5,6,7,8-octahydroisoquinoline from a racemic mixture, which involves treating partially resolved mixtures with a formic acid to form a nearly-racemic salt for further resolution.

1 Claim, 2 Drawing Sheets

SEPARATION OF ENANTIOMERS OF OCTAHYDROISOQUINOLINE

This application claims benefit of provisional application No. 60/059,193, filed Sep. 17, 1997.

BACKGROUND OF THE INVENTION

The 1-(p-methoxybenzyl)-1,2,3,4,5,6,7,8-octahydroisoquinoline (EP O 283 848 A1 [1988]):

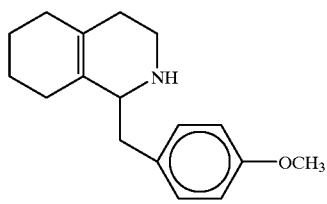

(I)

is an intermediate in the synthesis of compounds with morphinan type structure (Grewe, R.; Friedrichsen, W. Chem.Ber. 1967, 100, 1550.) The (−) enantiomer of I can be converted to dextromethorphan (Ger. Pat. 1795193 C2 (1971)), an important commercial antitussive agent. The (+) enantiomer can be used in the synthesis of levallorphan, a narcotic antagonist (Schneider, O.; Gruessner, D. Helv.Chim.Acta 1951 34,2211) or butorphanol, an analgesic (Ger. Pat. 2,2243, 961 (1973)).

When dextromethorphan is the target of the synthesis, the racemic I is subjected to enantiomeric resolution and the (−) enantiomer is converted to dextromethorphan. Usually, the enantiomeric resolution of I is done using diastereomeric salt precipitation with (−)-mandelic acid. The isolated material in the resolution step has an enantiomeric excess (ee) of 98–99% in (−) isomer. Left behind is a mixture which has a 60 to 70% ee in (+) isomer. Critical for the economics of the process is the recycling of this mixture. This is done by racemization of the (+) isomer, a chemically destructive process run under harsh conditions.

The object of this invention is a process of separation of the (−) enantiomer of I in which, in the recycling of the mixture after the separation of (−)-I, using (−)-mandelic acid, racemic I is isolated, and only (+)-I with ee of about 93–94% is subjected to the harsh, destructive conditions of the racemization step.

This and other objections of the invention will be apparent to one skilled in the art after review of the following description of the invention.

BRIEF DECSRIPTION OF THE DRAWINGS

THE INVENTION

Figure 1:
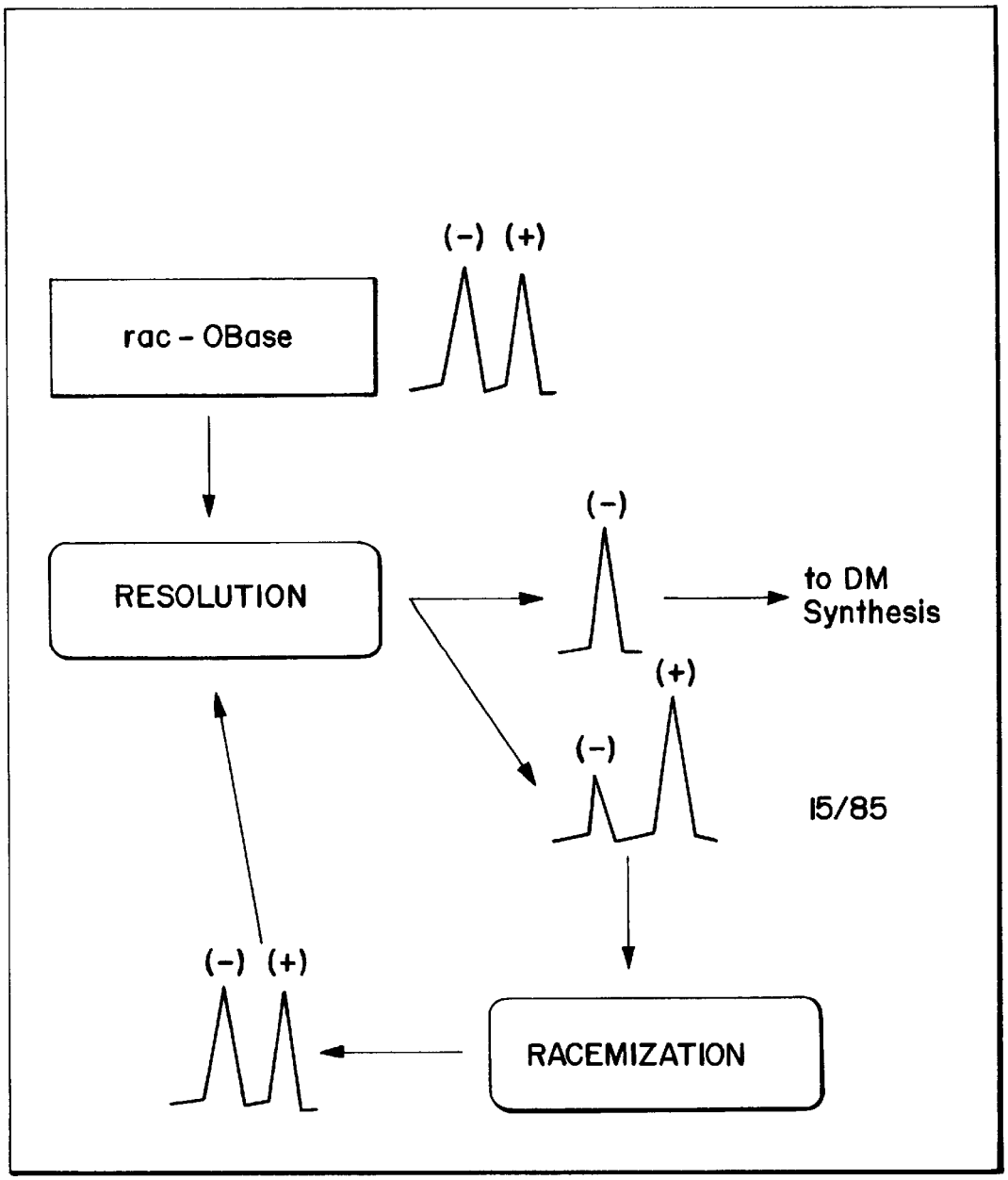
FIG. 1 is a flowchart showing existing process.

As hereinstated above, racemization the (+) isomer of 1-(p-methoxybenzyl)-1,2,3,4,5,6,7,8-octahydroisoquinoline (I) is a destructive process run under harsh conditions. FIG. 1 shows the existing process. The mixture after isolation of the (−) isomer of I still contains about 15–20% w/w (−) enantiomer. If this mixture is directed to racemization, this amount of (−) isomer is subjected needlessly to the harsh conditions of racemization.

The binary phase diagram of the formic acid salts of I show eutectic mixtures of composition close to the pure enantiomer. Subsequently, near racemic formic acid salt can be precipitated from a partially resolved mixture of (+)- and (−)-I. The racemic formate has a low solubility in toluene, which can be used as solvent. The optimum base substrate concentration in toluene is about 25 to about 45% w/w. The amount of formic acid added is from about 0.5 to about 1 molar equivalent, and the reaction temperature is isothermic at about 22–25 deg. C. The reaction time has no bearing on the yield, and can be from minutes to hours.

Figure 2:
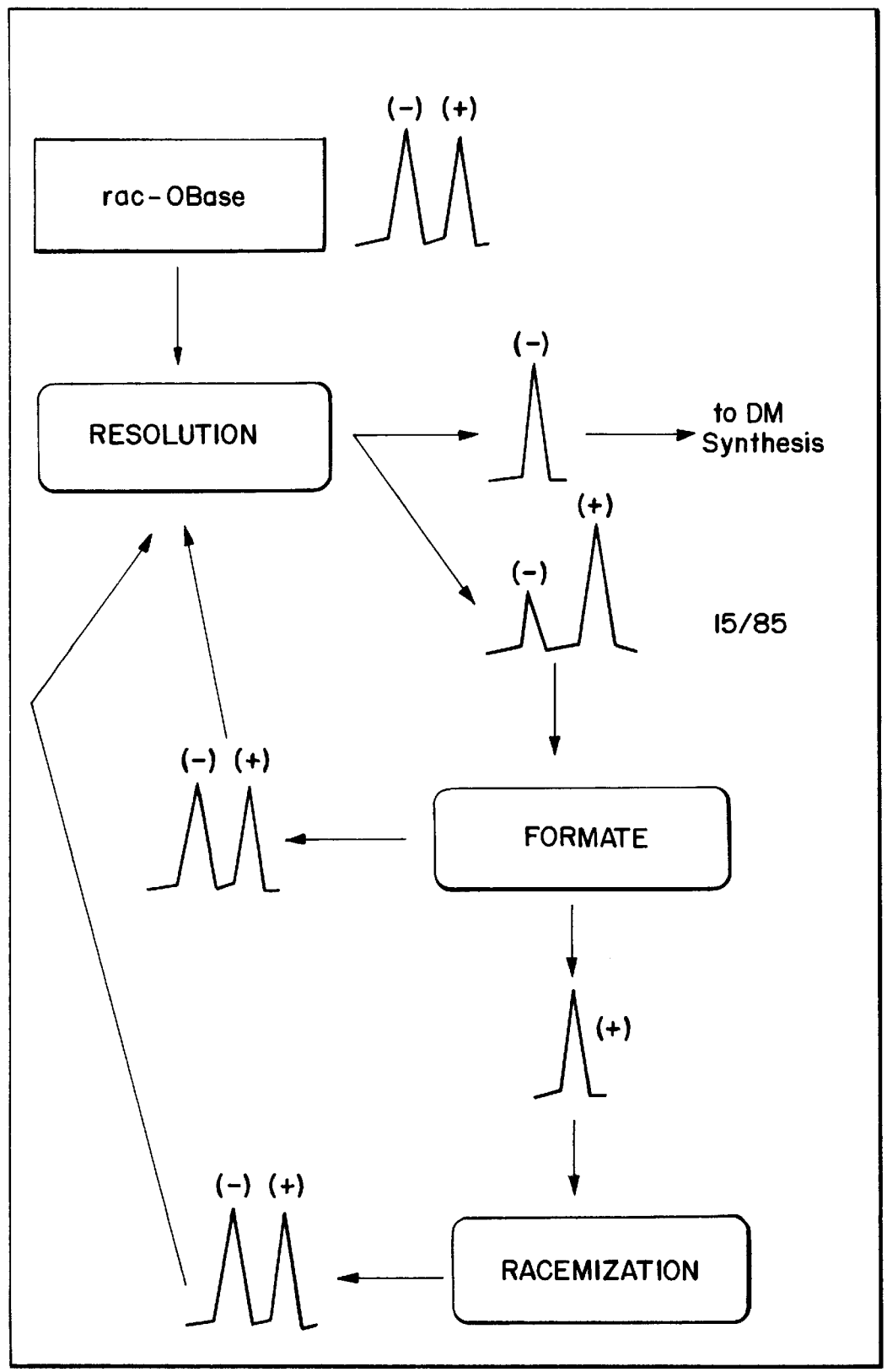
FIG. 2 is a flowchart showing process of present invention.

The isolation of the formic acid salt of racemic-I can be done after the racemization step as well, when it serves the purpose of purification. However, during the harsh racemization, considerable amounts of impurities are formed. The process of the present invention appears in FIG. 2.

EXAMPLE

To 75 g. toluene solution containing 21.75 g. I ( 0.0845 mol, 15.7% (−)-I and 84.3% (+)-I), 1.95 g. ( 0.0422 mol) formic acid is added dropwise, maintaining the temperature at about 22–24° C. The reaction mixture is stirred for about 1 hour. The solid is filtered, washed with toluene and dried. Yield: 7.1 g. (enantiomeric composition: 52.1% (+) yield 88.2% of theoretical). The mother liquor contains 3.22% (−)-I.

The enantiomeric composition was monitored by chiral HPLC.

The optimal parameters of the isolation of the formate of racemic-I were determined with respect to:

1. substrate concentration
2. formic acid amount
3. temperature
4. time

1. The dependence of the yield versus the concentration of the substrate in toluene, as determined experimentally, is presented in Table I:

TABLE I

| % Concentration: | % Yield: |
|---|---|
| 50 | 87.3 |
| 29.3 | 82.5 |
| 25 | 84.9 |
| 20 | 82.5 |
| 15 | 81.4 |
| 10 | 74.3 |
| 5 | 66.0 |

The yield increases with concentration. However, at concentration above about 50%, the solution is difficult to handle.

2. The minimum amount of formic acid is about 0.3 mol/mol I. With less formic acid, no precipitate is formed. The yield has a maximum at about 0.5 to about 1 mol/mol, as the data summarized in Table II show:

TABLE II

| Mol-ratio formic acid/I: | % Yield: |
|---|---|
| 0.3 | 82.5 |
| 0.5 | 83.7 |
| 0.75 | 83.7 |
| 1 | 83.7 |

TABLE II-continued

| Mol-ratio formic acid/I: | % Yield: |
|---|---|
| 1.25 | 82.5 |
| 1.5 | 69.6 |
| 2 | 0 (no ppt.) |

3. The temperature regimen should be isothermic i.e., the mixture should be cooled while adding the formic acid. If the mixture is allowed to warm from the exothermicity of the neutralization, the precipitate formed will be progressively farther from the racemic composition. This is illustrated in Table III:

TABLE III

| Substrate conc., % | Mol-ratio, formic acid/I: | Cooling, on/off: | Maximum temp. deg. C.: | % (+)-isomer in ppt.: |
|---|---|---|---|---|
| 29.3 | 1.0 | off | 42 | 54.8 |
| 50 | 1.0 | off | 70 | 57 |
| 30 | 1.0 | on | 22–24 isothermal | 52.1 |

There is no difference in yield between room temperature and about 5° C.

4. The effect of the reaction time was examined in the range of about 10 min. to about 18 hours. There was essentially no effect on the yield of precipitate detected.

What is claimed is:

1. In a process for the separation of (−)-enantiomer of

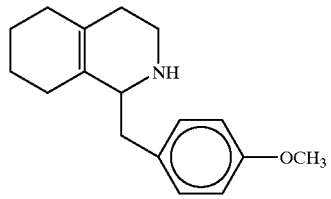

(I)

from a racemic mixture which involves resolution of the racemic mixture using (−)-mandelic acid to cause diastereometric salt formation with subsequent removal of the (−)-enantiomer-(−)mandelate and the resulting mother liquor having primarily (+)-enantiomer, the improvement which comprises treating the mother liquor with formic acid to form a racemic salt of low solubility, removing the racemic salt from the mother liquor by filtration and subjecting the racemic salt to resolution with (−)-mandelic acid.

* * * * *